(12) United States Patent
Hossainy et al.

(10) Patent No.: US 8,343,529 B2
(45) Date of Patent: *Jan. 1, 2013

(54) IMPLANTABLE DRUG DELIVERY DEVICES HAVING ALTERNATING HYDROPHILIC AND AMPHIPHILLIC POLYMER LAYERS

(75) Inventors: Syed F. A. Hossainy, Hayward, CA (US); Mikael O. Trollsas, San Jose, CA (US); Lothar W. Kleiner, Los Altos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/474,448

(22) Filed: May 17, 2012

(65) Prior Publication Data

US 2012/0225303 A1    Sep. 6, 2012

Related U.S. Application Data

(63) Continuation of application No. 12/130,162, filed on May 30, 2008, now Pat. No. 8,202,529.

(51) Int. Cl.
- *A61F 2/02* (2006.01)
- *B32B 27/08* (2006.01)
- *B32B 27/28* (2006.01)

(52) U.S. Cl. ............. 424/423; 424/423.5; 428/500; 428/423.1; 428/480; 428/476.3; 428/475.2; 428/510; 428/425.1; 428/481

(58) Field of Classification Search .................. None
See application file for complete search history.

(56) References Cited

U.S. PATENT DOCUMENTS

| | | | |
|---|---|---|---|
| 4,879,135 A | 11/1989 | Greco et al. | |
| 4,895,566 A | 1/1990 | Lee | |
| 5,993,972 A | 11/1999 | Reich et al. | |
| 6,398,758 B1 | 6/2002 | Jacobsen et al. | |
| 7,212,971 B2 | 5/2007 | Jost et al | |
| 7,225,518 B2 | 6/2007 | Eidenschink et al. | |
| 7,279,174 B2 | 10/2007 | Pacetti et al. | |
| 7,284,401 B2 | 10/2007 | Larson et al. | |
| 7,314,480 B2 | 1/2008 | Eidenschink et al. | |
| 7,645,504 B1 | 1/2010 | Pacetti | |
| 7,758,892 B1 | 7/2010 | Chen | |
| 7,794,495 B2 | 9/2010 | Gale et al. | |
| 2002/0103526 A1 | 8/2002 | Steinke | |
| 2004/0180039 A1 | 9/2004 | Toner et al. | |
| 2004/0215306 A1 | 10/2004 | Heil, Jr. et al. | |
| 2005/0004661 A1 | 1/2005 | Lewis et al. | |
| 2005/0147647 A1 | 7/2005 | Glauser et al. | |
| 2005/0165476 A1 | 7/2005 | Furst et al. | |
| 2005/0171596 A1 | 8/2005 | Furst et al. | |
| 2005/0181015 A1 | 8/2005 | Zhong | |
| 2005/0208100 A1 | 9/2005 | Weber et al. | |
| 2005/0232962 A1 | 10/2005 | Vrijhof | |
| 2005/0255142 A1 | 11/2005 | Chudzik et al. | |
| 2006/0160985 A1 | 7/2006 | Pacetti et al. | |
| 2006/0171895 A1 | 8/2006 | Bucay-Couto | |
| 2006/0171985 A1 | 8/2006 | Richard et al. | |
| 2006/0198869 A1 | 9/2006 | Furst et al. | |
| 2007/0003589 A1 | 1/2007 | Astafieva et al. | |
| 2007/0077271 A1 | 4/2007 | Dornish et al. | |
| 2007/0224244 A1 | 9/2007 | Weber et al. | |
| 2007/0254012 A1 | 11/2007 | Ludwig et al. | |
| 2009/0110711 A1 | 4/2009 | Trollsas et al. | |
| 2009/0297575 A1 | 12/2009 | Hossainy et al. | |

FOREIGN PATENT DOCUMENTS

| WO | WO 2004/069169 | 8/2004 |
|---|---|---|
| WO | WO 2005/115496 | 8/2005 |
| WO | WO 2009/148777 | 12/2009 |

OTHER PUBLICATIONS

U.S. Appl. No. 11/891,150, filed Aug. 8, 2007, Lee.
U.S. Appl. No. 11/899,740, filed Sep. 6, 2007, Hossainy et al.
U.S. Appl. No. 12/130,942, filed May 30, 2008, Hossainy et al.
U.S. Appl. No. 12/130,948, filed May 30, 2008, Hossainy et al.
U.S. Appl. No. 13/544,749, filed Jul. 9, 2012, Hossainy et al.
International Search Report for PCT/US2009/043650, mailed Aug. 17, 2010, 4 pgs.
Büllesfeld et al., "Long-term evaluation of paclitaxel-coated stents for treatment of native coronary lesions", Z. Kardiol 92, pp. 825-832 (2003).
Chao-Wei Hwang et al., "Physiological Transport Forces Govern Drug Distribution for Stent-Based Delivery", Circulation pp. 600-605 (2001).
Edward Roche Editor "Design of Biopharmaceutical Properties through Prodrugs and Analogs", Am. Pharma. Assoc. Academy of Pharm. Cciences, book, 4 title pages. (1977).
Grube et al., "Safety and Performance of a Paclitaxel Eluting Stent for the Treatment of In-Stent Restenosis: Preliminary Results of the Taxus III Trial", JACC Angiography & Interventional Cardiology, 1174-15 Abstract, pp. 58A-59A. (2002).
Grube et al., "Six-and Twelve-Month Results From a Randomized, Double-Blind Trial on a Slow-Release paclitaxel-eluting Stent for De Novo Coronary Lesions", Circulation vol. 7, No. 14, pp. 38-42 (2003).
Harper, "Drug Latentiation", Progress in Drug Research, 4:221-294 (1962).
Huh et al. "PLGA-PEG Block copolymers for Drug Formulations", Issue Date: vol. 3, No. 5 Jul./Aug. 2003, posted on: Mar. 28, 2008, 10 pgs.

(Continued)

*Primary Examiner* — Robert A Wax
*Assistant Examiner* — Danah Al-Awadi
(74) *Attorney, Agent, or Firm* — Squire Sanders (US) LLP

(57) ABSTRACT

An implantable drug delivery medical device with alternating hydrophilic and amphiphilic polymer layers and methods of using for the treatment of vascular disease are disclosed.

11 Claims, No Drawings

OTHER PUBLICATIONS

Lambert et al., "Localized Arterial Wall Drug Delivery From a Polymer-Coated Removable Metallic Stent", Circulation vol. 90, No. 2, pp. 1003-1011 (1994).

Lincoff et al., "Sustained Local Delivery of Dexamethasone by a Novel Intravascular Eluting Stent to Prevent Restenosis in the Porcine Coronary Injury Model", JACC vol. 29, No. 4, pp. 808-816 (1997).

Miller-Chou et al., "A review of polymer dissolution", Prog. Polym. Sci. 28, pp. 1223-1270 (2003).

Sankalia et al., "Reversed chitosan-alginate polyeslectrolyte complex for stability improvement of alpha-amylase: Optimization and physicochemical characterization", Eu J. of Pharm. and Biopharmaceutics 65, pp. 215-232 (2007).

Sinkula et al., "Rationale for Design of Biologically Reversible Drug Derivatives: Prodrugs", J. of Pharm. Science vol. 64, No. 2, pp. 181-210 (1975).

Stella et al. "Prodrugs—Do they Have Advantages in Clinical Practice?", Drugs 29, pp. 455-473 (1985).

Tanabe et al., "In-Stent Restenosis Treated with Stent-Based Delivery of Paclitaxel Incorporated in a Slow-Release Polymer Formulation", Circulation, pp. 559-564 (2003).

Van der Giessen et al., "Marked Inflammatory Sequelae to Implantation of Biodegradable and Nonbiodegradable Polymers in Porcine Coronary Arteries", Circulation vol. 94, No. 7, pp. 1690-1697 (1996).

Zhang et al., "Natural polyelectrolyte films based on layer-by layer deposition of collagen and hyaluronic acid", Biomaterials 26, pp. 3353-3361 (2005).

IMPLANTABLE DRUG DELIVERY DEVICES HAVING ALTERNATING HYDROPHILIC AND AMPHIPHILLIC POLYMER LAYERS

CROSS-REFERENCE TO RELATED APPLICATIONS

This application is a continuation of U.S. application Ser. No. 12/130,162, filed on May 30, 2008, published as United States Patent Application Publication No. 2009-0297575 A1 on Dec. 3, 2009, and issuing as U.S. Pat. No. 8,202,529 on Jun. 19, 2012, which is incorporated by reference herein in its entirety, including any drawings.

FIELD OF THE INVENTION

The present invention is directed to implantable drug delivery devices with alternating hydrophilic and amphiphilic polymer layers.

BACKGROUND OF THE INVENTION

Systemic delivery is the traditional method of administering therapeutic agents to treat diseases of the internal organs and vasculature. Systemic delivery involves administering a therapeutic agent at a discrete location followed by the agent migrating throughout the patient's body including, of course, to the afflicted organ or area of the vasculature. But to achieve a therapeutic amount of the agent at the afflicted site, an initial dose substantially greater than the therapeutic amount must be administered to account for the dilution the agent undergoes as it travels through the body. Systemic delivery introduces the therapeutic agent in two ways: into the digestive tract (enteral administration) or into the vascular system (parenteral administration), either directly, such as injection into a vein or an artery, or indirectly, such as injection into a muscle or into the bone marrow. Absorption, distribution, metabolism, excretion and toxicity, the ADMET factors, strongly influence delivery by each of these routes. For enteric administration, factors such as a compound's solubility, its stability in the acidic environs of the stomach and its ability to permeate the intestinal wall all affect drug absorption and therefore its bioavailability. For parenteral delivery, factors such as enzymatic degradation, lipophilic/hydrophilic partitioning coefficient, lifetime in circulation, protein binding, etc. will affect the agent's bioavailability.

At the other end of the spectrum is local delivery, which comprises administering the therapeutic agent directly to the afflicted site. With localized delivery, the ADMET factors tend to be less important than with systemic administration because administration is essentially directly to the treatment site. Thus, the initial dose can be at or very close to the therapeutic amount. With time, some of the locally delivered therapeutic agent may diffuse over a wider region, but that is not the intent of localized delivery, and the diffused portion's concentration will ordinarily be sub-therapeutic, i.e., too low to have a therapeutic effect. Nevertheless, localized delivery of therapeutic agents is currently considered a state-of-the-art approach to the treatment of many diseases such as cancer and atherosclerosis.

Localized delivery of therapeutic agents may be accomplished using implantable medical devices, e.g., drug-eluting stents (DESs). In fact, DESs coated with antiproliferative and/or anti-inflammatory drugs are currently considered one of the most effective means of combating restenosis.

The efficacy of DESs is related to their ability to release drugs in a controlled manner. One way this is accomplished is by putting drugs in a drug reservoir layer that includes a polymeric matrix that mediates the release rate of the drug. Another way is to include on the DES a rate-controlling layer that is disposed over a drug reservoir layer and which comprises one or more polymers selected for their ability to mediate release of a particular drug or drugs from the underlying reservoir layer.

What is lacking in the art, however, are readily soluble polymer layers which allow for both the controlled release of drug as well as the sustained degradation of the polymer layers.

SUMMARY OF THE INVENTION

The present invention relates to an implantable medical device that includes a device body and a soluble coating wherein the soluble coating includes a primer layer disposed over the device body, wherein the primer layer comprises either a hydrophilic polymer or an amphiphilic polymer and a reservoir layer disposed over the primer layer, wherein if the primer layer comprises a hydrophilic polymer the reservoir layer comprises an amphiphilic polymer or alternatively if the primer layer comprises an amphiphilic polymer the reservoir layer comprises a hydrophilic polymer. Also present is a topcoat layer disposed over the reservoir layer, wherein if the reservoir layer comprises a hydrophilic polymer the topcoat layer comprises an amphiphilic polymer or alternatively if the reservoir layer comprises an amphiphilic polymer the topcoat layer comprises a hydrophilic polymer. The soluble coating solvates completely within about 30 days after deployment of the implantable medical device. In preferred embodiments the device body is a soluble stent, a metal stent or a bare polymer stent.

In various aspects, the metal stent material can be selected from a group that includes stainless steel, nitinol, tantalum, tantalum alloy, titanium, titanium alloy, cobalt chromium, nickel chromium iron alloy, niobium, niobium alloy, zirconium and zirconium alloy.

In various aspects, the hydrophilic polymer can be selected from a group that includes polyvinylpyrrolidone, poly(carboxymethyl cellulose) and poly[N-(2-hydroxypropyl)methacrylamide].

In various aspects, the amphiphilic polymer can be selected from a group that includes poly(n-butyl methacrylate-phosphorylcholine), poly(ester amide)-phosphorylcholine, polylactide-phosphorylcholine, polyethylene glycol-poly(caprolactone)-di- or tri-blocks, polyethylene glycol-polylactide di- or tri-blocks and polyethylene glycol-poly(lactide-glycolide) di- or tri-blocks.

In various aspects, the reservoir layer can include one or more bioactive agents selected from a group that includes an antiproliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cyto-protective agent, a cardioprotective agent, a proliferative agent, an ABCA1 agonist and an antioxidant or any combination thereof.

In certain aspects, an implantable medical device of the invention can further include a rate-controlling layer disposed over the drug reservoir layer, wherein if the reservoir layer comprises a hydrophilic polymer the rate-controlling layer comprises an amphiphilic polymer and the topcoat layer comprises a hydrophilic polymer, or alternatively if the reservoir layer comprises an amphiphilic polymer the rate-controlling layer comprises a hydrophilic polymer and the topcoat layer comprises an amphiphilic polymer.

In various aspects, the soluble coating solvates completely within about 14 days or within about 1 to 3 days after deployment of the implantable medical device.

In various aspects, about 80% of the bioactive agent releases from the soluble coating within about 1 to 3 days after deployment of the implantable medical device.

Another aspect of the invention relates to a soluble coating for an implantable medical device that includes a primer layer that includes either a hydrophilic polymer or an amphiphilic polymer and a reservoir layer disposed over the primer layer, wherein if the primer layer comprises a hydrophilic polymer the reservoir layer comprises an amphiphilic polymer or alternatively if the primer layer comprises an amphiphilic polymer the reservoir layer comprises a hydrophilic polymer. Also present is a topcoat layer disposed over the reservoir layer, wherein if the reservoir layer comprises a hydrophilic polymer the topcoat layer comprises an amphiphilic polymer, or alternatively if the reservoir layer comprises an amphiphilic polymer the topcoat layer comprises a hydrophilic polymer. The soluble coating solvates completely within about 30 days after deployment of the implantable medical device.

In various aspects, the hydrophilic polymer can be selected from a group that includes polyvinylpyrrolidone, poly(carboxymethyl cellulose) and poly[N-(2-hydroxypropyl)methacrylamide].

In various aspects, the amphiphilic polymer can be selected from a group that includes poly(n-butyl methacrylate-phosphorylcholine), poly(ester amide)-phosphorylcholine, polylactide-phosphorylcholine, polyethylene glycol-poly(caprolactone)-di- or tri-blocks, polyethylene glycol-polylactide di- or tri-blocks and polyethylene glycol-poly(lactide-glycolide) di- or tri-blocks.

In various aspects, the reservoir layer can include one or more bioactive agents selected from a group that includes an antiproliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cyto-protective agent, a cardioprotective agent, a proliferative agent, an ABC A1 agonist and an antioxidant or any combination thereof.

In certain aspects, a soluble coating of the invention can further include a rate-controlling layer disposed over the drug reservoir layer, wherein if the reservoir layer comprises a hydrophilic polymer the rate-controlling layer comprises an amphiphilic polymer and the topcoat layer comprises a hydrophilic polymer, or alternatively if the reservoir layer comprises an amphiphilic polymer the rate-controlling layer comprises a hydrophilic polymer and the topcoat layer comprises an amphiphilic polymer.

Another aspect of the present invention relates to a method for treating or preventing a vascular disease comprising implanting a medical device according to the invention in a vessel of a patient in need thereof. The vascular disease to be treated can be atherosclerosis, restenosis, vulnerable plaque or peripheral arterial disease.

Another aspect of the present invention relates to a soluble implantable medical device comprising alternating layers of hydrophilic and amphiphilic polymers.

In various aspects, the hydrophilic polymer can be selected from a group that includes polyvinylpyrrolidone, poly(carboxymethyl cellulose) and poly[N-(2-hydroxypropyl)methacrylamide].

In various aspects, the amphiphilic polymer can be selected from a group that includes poly(n-butyl methacrylate-phosphorylcholine), poly(ester amide)-phosphorylcholine, polylactide-phosphorylcholine, polyethylene glycol-poly(caprolactone)-di- or tri-blocks, polyethylene glycol-polylactide di- or tri-blocks and polyethylene glycol-poly(lactide-glycolide) di- or tri-blocks.

In various aspects, the implantable medical device can further include one or more bioactive agents integrated into the structure of or adhered to the surface of the device.

In various aspects, the one or more bioactive agents can be selected from a group that includes an antiproliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cyto-protective agent, a cardioprotective agent, a proliferative agent, an ABC A1 agonist or an antioxidant or any combination thereof.

Another aspect of the present invention relates to a method for fabricating an implantable medical device that includes a soluble coating. The method involves providing a device body, disposing a primer layer over the device body wherein the primer layer comprises either a hydrophilic polymer or an amphiphilic polymer, disposing a reservoir layer over the primer layer, wherein if the primer layer comprises a hydrophilic polymer the reservoir layer comprises an amphiphilic polymer or alternatively if the primer layer comprises an amphiphilic polymer the reservoir layer comprises a hydrophilic polymer and disposing a topcoat layer over the reservoir layer, wherein if the reservoir layer comprises a hydrophilic polymer the topcoat layer comprises an amphiphilic polymer or alternatively if the reservoir layer comprises an amphiphilic polymer the topcoat layer comprises a hydrophilic polymer.

In various aspects, the device body is a soluble stent, a metal stent or a bare polymer stent. In certain aspects, the metal stent material can be selected from a group that includes stainless steel, nitinol, tantalum, tantalum alloy, titanium, titanium alloy, cobalt chromium, nickel chromium iron alloy, niobium, niobium alloy, zirconium and zirconium alloy.

In various aspects, the hydrophilic polymer can be selected from a group that includes polyvinylpyrrolidone, poly(carboxymethyl cellulose) and poly[N-(2-hydroxypropyl)methacrylamide].

In various aspects, the amphiphilic polymer can be selected from a group that includes poly(n-butyl methacrylate-phosphorylcholine), poly(ester amide)-phosphorylcholine, polylactide-phosphorylcholine, polyethylene glycol-poly(caprolactone)-di- or tri-blocks, polyethylene glycol-polylactide di- or tri-blocks and polyethylene glycol-poly(lactide-glycolide) di- or tri-blocks.

In various aspects, the reservoir layer can include one or more bioactive agents selected from a group that includes an antiproliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cyto-protective agent, a cardioprotective agent, a proliferative agent, an ABC A1 agonist and an antioxidant or any combination thereof.

In various aspects, the method can further involve disposing a rate-controlling layer over the drug reservoir layer, wherein if the reservoir layer comprises a hydrophilic polymer the rate-controlling layer comprises an amphiphilic polymer and the topcoat layer comprises a hydrophilic polymer or alternatively if the reservoir layer comprises an amphiphilic polymer the rate-controlling layer comprises a hydrophilic polymer and the topcoat layer comprises an amphiphilic polymer.

DETAILED DESCRIPTION

The present invention relates to an implantable medical device coated with alternating hydrophilic and amphiphilic polymer layers. The design allows the coating to be soluble in vivo, thereby allowing for sustained drug release and efficient biodegradation of the coating.

As used herein, "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators, leads and electrodes for the preceding, implantable organ stimulators such as nerve, bladder, sphincter and diaphragm stimulators, cochlear implants, prostheses, vascular grafts, self-expandable stents, balloon-expandable stents, stent-grafts, grafts, PFO closure devices, arterial closure devices, artificial heart valves and cerebrospinal fluid shunts. Presently preferred implantable medical devices include stents, including soluble stents, metal stents and bare polymer-based stents, examples of which are known to those skilled in the art.

A stent refers generally to any device used to hold tissue in place in a patient's body. Particularly useful stents are those used for the maintenance of the patency of a vessel in a patient's body when the vessel is narrowed or closed due to diseases or disorders including, without limitation, tumors (in, for example, bile ducts, the esophagus or the trachea/bronchi), benign pancreatic disease, coronary artery disease, carotid artery disease, renal artery disease and peripheral arterial disease such as atherosclerosis, restenosis and vulnerable plaque. For example, a stent can be used to strengthen the wall of the vessel in the vicinity of a vulnerable plaque (VP). VP refers to a fatty build-up in an artery thought to be caused by inflammation. The VP is covered by a thin fibrous cap that can rupture leading to blood clot formation. Thus, a stent can not only maintain vessel patency but can act as a shield against VP rupture. A stent can be used in, without limitation, neuro, carotid, coronary, pulmonary, aortic, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. Indeed, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. Due to the expansion of the stent, however, a stent coating must be flexible and capable of elongation.

Exemplary metal stent materials include, without limitation, stainless steel, nitinol, tantalum, tantalum alloy, titanium, titanium alloy, cobalt chromium, nickel chromium iron alloy, niobium, niobium alloy, zirconium and zirconium alloy. Exemplary bare polymer stent materials and soluble stent materials are known to those skilled in the art.

As used herein, "device body" refers to a fully formed implantable medical device with an outer surface to which no coating or layer of material different from that of which the device itself is manufactured has been applied. "Outer surface" means any surface, however spatially oriented, that is in contact with bodily tissue or fluids. An example of a "device body" is a BMS, i.e., a bare metal stent, which is a fully-formed usable stent that has not been coated with a layer of any material different from the metal of which it is made. It is to be understood that device body refers not only to BMSs but also to any uncoated device regardless of what it is made.

As used herein, "primer layer" refers to a coating consisting of a polymer or blend of polymers that exhibit good adhesion characteristics with regard to the material of which the device body is manufactured and good adhesion characteristics with regard to whatever material is to be coated on the device body. A primer layer is applied directly to a device body to serve as an intermediary layer between the device body and materials to be affixed to the device body. Primer layers of the invention will necessarily comprise either a hydrophilic polymer or alternatively an amphiphilic polymer, the choice of which will be left up to the practitioner.

Exemplary hydrophilic polymers can be selected from a group that includes, without limitation, polyvinylpyrrolidone, poly(carboxymethyl cellulose) and poly[N-(2-hydroxypropyl)methacrylamide].

Exemplary amphiphilic polymers can be selected from a group that includes, without limitation, poly(n-butyl methacrylate-phosphorylcholine), poly(ester amide)-phosphorylcholine, polylactide-phosphorylcholine, polyethylene glycol-poly(caprolactone)-di- or tri-blocks, polyethylene glycol-polylactide di- or tri-blocks and polyethylene glycol-poly(lactide-glycolide) di- or tri-blocks. It is to be understood, however, that any amphiphilic polymer that can be made from hydrophobic and hydrophilic subunits is also encompassed by the present invention and such polymers will be easily discernable by those skilled in the art.

For the present invention, whether a material is hydrophilic or hydrophobic will be relative. Between different materials, whichever has a lower Hildebrand value (d) value compared to the d value of the other is designated as hydrophobic, and the material with a higher Hildebrand value (d) value is designated as hydrophilic. A d value defining the boundary between hydrophobic and hydrophilic can be between about 9.9 and 10.1 $(cal/cm^3)^{1/2}$. According to the invention, hydrophobic is defined as having a d value equal to or below about 9.9 $(cal/cm^3)^{1/2}$, and hydrophilic is defined as having a d value of about 10.1 $(cal/cm^3)^{1/2}$ or higher. Materials having a d value between about 9.9 and 10.1 $(cal/cm^3)^{1/2}$ can exhibit behavior characterized by both hydrophilic and hydrophobic materials. Such materials are defined as "amphiphilic." Measurements other than Hildebrand value for the determination of hydrophobicity are known to those skilled in the art and may be employed in the same manner as the Hildebrand value to achieve the same end.

According to the invention, a hydrophilic or amphiphilic polymer primer layer will be disposed over a device body.

As used herein, a material that is described as a layer "disposed over" an indicated substrate, e.g., a stent or another layer, refers to a relatively thin coating of the material applied directly to essentially the entire exposed surface of the indicated substrate. The term "disposed over" may, however, also refer to the application of the thin layer of material to an intervening layer that has been applied to the substrate, wherein the material is applied in such a manner that, were the intervening layer not present, the material would cover substantially the entire exposed surface of the substrate.

Methods of disposing layers over the device and over other layers include, without limitation, dip-coating, spray coating (including electrospray coating), powder coating, using an ink jet and other techniques known to those skilled in the art.

For example, layers can be disposed over a device by dissolving a coating composition, e.g., a hydrophilic or amphiphilic polymer, in a solvent or a mixture of solvents, and disposing the resulting solution over the stent by spraying or immersing the stent in the solution. The coating can then be dried by allowing the solvent to evaporate. Drying can be accelerated by the application of heat. In addition to just the layers being dried, the whole stent coating can be optionally annealed at a temperature between about 40° C. and about 150° C., e.g., 80° C., for a period of time between about 5 minutes and about 60 minutes thereby allowing for crystallization of the coating which can improve the thermodynamic stability of the coating.

As used herein, "reservoir layer" refers to a layer applied to the primer layer that has dispersed within its three-dimensional structure one or more therapeutic agents. A reservoir layer is designed such that, without limitation, by elution or as the result of biodegradation of the polymer, the therapeutic substance is released from the layer into the surrounding environment. It is to be understood that the material of which the primer layer is composed with dictate the material of which the reservoir layer is composed. For example, if the primer layer is composed of a hydrophilic polymer then the reservoir layer will be composed of an amphiphilic polymer. Alternatively, if the primer layer is composed of an amphiphilic polymer then the reservoir layer will be composed of a hydrophilic polymer. Exemplary hydrophilic and amphiphilic polymers are described above, although other polymers known or that will be known to those skilled in the art are encompassed by the present invention.

To incorporate one or more bioactive agents into the reservoir layer, examples of which are described below, the agent can be combined with the reservoir layer coating solution that is to be disposed over the implantable medical device, as described above. Alternatively, instead of introducing an agent via a solution, the agent can be introduced as a colloid system, such as a suspension in an appropriate solvent phase using techniques known to those skilled in the art.

It is also understood that the hydrophilic and amphiphilic polymers of the invention will be biocompatible.

As used herein, "biocompatible" refers to a polymer that both in its intact, as synthesized state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

In addition to either the hydrophilic or amphiphilic polymer, the reservoir layer contains one or more bioactive agents which can be released from the medical device after implantation.

It is understood that the agent will have a release profile which can be the same or different from the solvation profile of the soluble polymer layers but that no agent would remain after all the soluble polymer layers have dissolved. Specifically, the soluble coatings of the invention will completely solvate, that is dissolve, within about 30 days after deployment of the implantable medical device, yet in some situations the coatings can completely solvate within about 14 days or within about 1 to 3 days after deployment of an implantable medical device with such a coating depending on the needs of the practitioner. With respect to the release of bioactive agent, in preferred embodiments about 80% of bio active agent will be released from a soluble coating of the invention within about 1 to 3 days after deployment of the implantable medical device.

The bioactive agent, also referred to herein as a drug or therapeutic agent, can include, without limitation, an antiproliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cyto-protective agent, a cardioprotective agent, a proliferative agent, an ABC A1 agonist or an antioxidant or any combination thereof.

Examples of antiproliferative agents include, without limitation, actinomycin D, or derivatives or analogs thereof, e.g., actinomycin $I_1$, actinomycin actinomycin $X_1$, and actinomycin $C_1$. Antiproliferative agents can be natural proteineous agents such as cytotoxins or they can be natural or synthetic small molecules such as, without limitation, taxoids such as taxols, docetaxel, paclitaxel and paclitaxel derivatives, macrolide compounds such as, without limitation, rapamycin and derivative and analogs thereof such as everolimus, biolimus and tacrolimus and derivatives of any of the foregoing perfenidone and prodrugs and co-drugs of any of the foregoing thereof as well as combinations of any of these. Additional rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, prodrugs thereof, co-drugs thereof and combinations thereof.

Examples of anti-inflammatory agents include, without limitation, steroidal and nonsteroidal anti-inflammatory compounds such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin, salicylic acid, corticosteroids, glucocorticoids, tacrolimus, pimecrolimus, prodrugs, co-drugs and combinations thereof. The anti-inflammatory agent may also be a biological inhibitor of proinflammatory signaling molecules such as antibodies that bind to such signaling molecules.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax™ (bivalirudin, Biogen, Inc., Cambridge, Mass.), calcium channel blockers (such as nifedipine), colchicine, fish oil (omega 3-fatty acid), histamine antagonists, lovastatin, monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as vitamins, and combinations thereof.

An example of an antiallergic agent is permirolast potassium.

Other bioactive agents that may be useful include alpha-interferon and genetically engineered epithelial cells.

Examples of potentially useful cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (omega-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids and thioprotease inhibitors.

Some additional potentially useful bioactive agents include, without limitation, any bioactive synthetic inorganic and organic compounds, proteins and peptides, polysaccharides and other sugars, lipids, and DNA and RNA nucleic acid sequences having therapeutic, prophylactic or diagnostic activities, nucleic acid sequences include genes, antisense molecules which bind to complementary DNA to inhibit transcription, ribozymes, antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

The dosage or concentration of bioactive agent should be less than the level at which the agent produces a toxic effect and greater than the level at which therapeutic results would not be obtained. The dosage or concentration can depend upon the particular circumstances of the patient, the nature of the trauma, the nature of the therapy desired, the time over which the ingredient administered resides at the vascular site and if more than one agent is used the nature and type of the combination of agents. Therapeutically effective dosages can be determined empirically, for example by infusing vessels from suitable animal model systems and using immunohistochemical, fluorescent or electron microscopy to detect the agent and its effects or by conducting suitable in vitro studies.

An implantable medical device of the invention will also include a top-coat layer disposed over the reservoir layer. As used herein, "top-coat layer" refers to an outermost layer that is in contact with the external environment and that is disposed as the final layer of a series of layers. The topcoat layer is disposed over the reservoir layer of the invention, and in some cases a rate-controlling layer. The topcoat layer will be composed of a hydrophilic polymer if the reservoir layer is composed of an amphiphilic polymer or alternatively an amphiphilic polymer if the reservoir layer is composed of a hydrophilic polymer. Exemplary hydrophilic and amphiphilic polymers are described above.

In certain situations, a rate-controlling layer will be disposed over the reservoir layer and under the topcoat layer. As used herein, "rate-controlling layer" refers to a polymeric layer that is applied over a drug reservoir layer to modify a bioactive agent's rate of release into the environment. A rate-controlling layer may be used simply to "tune" the rate of release to exactly that desired by the practitioner or it may be a necessary adjunct to the construct because the polymer or blend of polymers with which the bioactive agent is compatible, with regard to coating as a drug reservoir layer, may be too permeable to the bioactive substance resulting in too rapid release and delivery of the bioactive substance into a patient's body.

If the reservoir layer is composed of a hydrophilic polymer then the rate-controlling will be composed of an amphiphilic polymer and the topcoat layer will be composed of a hydrophilic polymer. Alternatively, if the reservoir layer is composed of an amphiphilic layer then the rate-controlling layer will be composed of a hydrophilic layer and the topcoat layer will be composed of an amphiphilic layer.

Another aspect of the invention relates to a soluble coating for an implantable medical device that includes a primer layer comprising either a hydrophilic polymer or an amphiphilic polymer and a reservoir layer disposed over the primer layer, wherein if the primer layer comprises a hydrophilic polymer the reservoir layer comprises an amphiphilic polymer or alternatively if the primer layer comprises an amphiphilic polymer the reservoir comprises a hydrophilic polymer. Also present is a topcoat layer disposed over the reservoir layer, wherein if the reservoir layer comprises a hydrophilic polymer the topcoat layer comprises an amphiphilic polymer, or alternatively if the reservoir layer comprises an amphiphilic polymer the topcoat layer comprises a hydrophilic polymer.

As used herein, "soluble coating" refers to a coating that is capable of being completely or substantially degraded, dissolved and/or eroded over time when exposed to physiological conditions, e.g., the conditions at the site of device implantation. The process of coating degradation, dissolving and/or erosion can be caused by, for example, hydrolysis, metabolic processes, oxidation, enzymatic processes and/or bulk or surface erosion. As discussed above, soluble coatings of the invention will solvate completely within about 30 days after deployment of the implantable medical device and in certain situations within about 14 days or within about 1 to 3 days after deployment of an implantable medical device with such a coating.

Exemplary hydrophilic and amphiphilic polymers are described above.

In certain aspects, a soluble coating of the invention can further include a rate-controlling layer disposed over the drug reservoir layer. When the reservoir layer is composed of a hydrophilic polymer the rate-controlling layer can be composed of an amphiphilic polymer and the topcoat layer can be composed of a hydrophilic polymer. Alternatively, if the reservoir layer comprises an amphiphilic polymer the rate-controlling layer comprises a hydrophilic polymer and the topcoat layer comprises an amphiphilic polymer.

Another aspect of the invention relates to a method for treating or preventing a vascular disease. The method involves implanting a medical device of the invention in a vessel of a patient in need thereof. The vascular disease to be treated includes atherosclerosis, restenosis, vulnerable plaque and peripheral arterial disease. It is to be understood, however, that the methods of the invention can also be used to treat, without limitation, thrombosis, hemorrhage, vascular dissection, vascular perforation, vascular aneurysm, chronic total occlusion, patent foramen ovale, claudication, anastomotice proliferation of vein and artificial grafts, arteriovenous anastomoses, bile duct obstruction, ureter obstruction and tumor obstruction.

Methods of implanting medical devices are known to those skilled in the art.

As used herein, "treating" refers to the administration of a therapeutically effective amount of a drug to a patient known or suspected to be suffering from a vascular disease.

As used herein, "therapeutically effective amount" refers to the amount of drug that has a beneficial effect, which may be curative or palliative, on the health and well-being of a patient with regard to a vascular disease with which the patient is known or suspected to be afflicted. A therapeutically effective amount may be administered as a single bolus, as intermittent bolus charges, as short, medium or long term sustained release formulations or as any combination of these.

As used herein, "known" to be afflicted with a vascular disease refers first to a condition that is relatively readily observable and or diagnosable. An example, without limitation, of such a disease is atherosclerosis, which is a discrete narrowing of a patient's arteries. Restenosis, on the other hand, while in its latter stages, like atherosclerosis, is relatively readily diagnosable or directly observable, may not be so in its nascent stage. Thus, a patient may be "suspected" of being afflicted or of being susceptible to affliction with restenosis at some time subsequent to a surgical procedure to treat an atherosclerotic lesion. Further, while restenosis tends generally to occur at the same locus as a previous atherosclerotic lesion, it may not be exactly so, so a region of a segment of a vessel somewhat distant from the site of the initial atherosclerosis may in fact be the site of restenosis.

As used herein, a "vascular disease locale" refers to the location within a patient's body where an atherosclerotic lesion(s) is present, where restenosis may develop, the site of vulnerable plaque(s) or the site of a peripheral arterial disease.

An atherosclerotic lesion refers to a deposit of fatty substances, cholesterol, cellular waste products, calcium and/or fibrin on the inner lining or intima of an artery.

Restenosis refers to the re-narrowing or blockage of an artery at or near the site where angioplasty or another surgical or interventional procedure was previously performed to remove a stenosis.

Vulnerable plaque on the other hand is quite different from either atherosclerosis or restenosis and would generally come under the designation "suspected" affliction. This is because vulnerable plaque occurs primarily within the wall of a vessel and does not cause prominent protrusions into the lumen of the vessel. It is often not until it is "too late," i.e., until after a vulnerable plaque has broken and released its components into the vessel, that its presence is even known. Numerous methods have and are being investigated for the early diagnosis of vulnerable plaque but to date none have proven completely successful. Thus, the regional treatment of a segment of a vessel suspected of being afflicted with vulnerable plaque may be the best way to address such lesions.

As used herein, "peripheral arterial disease" refers to a condition similar to coronary artery disease and carotid artery disease in which fatty deposits build up in the inner linings of the artery walls thereby restricting blood circulation, mainly in arteries leading to the kidneys, stomach, arms, legs and feet.

Another aspect of the present invention relates to a soluble implantable medical device that is composed of alternating layers of hydrophilic and amphiphilic polymers. Exemplary hydrophilic and amphiphilic polymers are described above. Methods of fabricating such a device are found in U.S. Publication No. US/2007/0254012 which is herein incorporated by reference in its entirety.

In various aspects, the soluble implantable medical device can further include one or more bioactive agents integrated into the structure of or adhered to the surface of the device.

As used herein, "integrated into the structure of" means the bioactive agent is part of the chemical structure of the polymer material.

As used herein, "adhered to the surface of" means the bioactive agent is covalently or non-covalently attached to the outer surface of the device.

Exemplary Bioactive Agents Are Described Above.

Another aspect of the present invention relates to a method for fabricating an implantable medical device with a soluble coating. The method involves providing a device body, disposing a primer layer over the device body wherein the primer layer comprises either a hydrophilic polymer or an amphiphilic polymer, disposing a reservoir layer over the primer layer, wherein if the primer layer comprises a hydrophilic polymer the reservoir layer comprises an amphiphilic polymer or alternatively if the primer layer comprises an amphiphilic polymer the reservoir layer comprises a hydrophilic polymer and disposing a topcoat layer over the reservoir layer, wherein if the reservoir layer comprises a hydrophilic polymer the topcoat layer comprises an amphiphilic polymer or alternatively if the reservoir layer comprises an amphiphilic polymer the topcoat layer comprises a hydrophilic polymer. Exemplary device bodies are described above. Exemplary hydrophilic polymers are described above. Exemplary amphiphilic polymers are described above. Exemplary bioactive agents are described above.

In various aspects, the method can further involve disposing a rate-controlling layer over the drug reservoir layer, wherein if the reservoir layer comprises a hydrophilic polymer the rate-controlling layer comprises an amphiphilic polymer and the topcoat layer comprises a hydrophilic polymer or alternatively if the reservoir layer comprises an amphiphilic polymer the rate-controlling layer comprises a hydrophilic polymer and the topcoat layer comprises an amphiphilic polymer. Methods of disposing any of the above-mentioned layers over a device body are described above.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A soluble implantable medical device comprising alternating layers of hydrophilic and amphiphilic polymers;
    wherein the amphiphilic polymer is selected from the group consisting of poly(n-butyl methacrylate-phosphorylcholine), poly(ester amide)-phosphorylcholine, polylactide-phosphorylcholine, polyethylene glycol-poly(caprolactone)-di- or tri-blocks, polyethylene glycol-polylactide di- or tri-blocks and polyethylene glycol-poly(lactide-glycolide) di- or tri-blocks.

2. The implantable medical device according to claim 1, wherein the hydrophilic polymer is selected from the group consisting of polyvinylpyrrolidone, poly(carboxymethyl cellulose) and poly[N-(2-hydroxypropyl)methacrylamide].

3. The implantable medical device according to claim 1, further comprising one or more bioactive agents integrated into the structure of or adhered to the surface of the device.

4. The implantable medical device according to claim 3, wherein the one or more bioactive agents are selected from the group consisting of an antiproliferative agent, an anti-inflammatory agent, an antineoplastic, an antimitotic, an anti-platelet, an anticoagulant, an antifibrin, an antithrombin, a cytostatic agent, an antibiotic, an anti-allergic agent, an anti-enzymatic agent, an angiogenic agent, a cyto-protective agent, a cardioprotective agent, a proliferative agent, an ABC A1 agonist, an antioxidant, and combinations thereof.

5. The implantable medical device according to claim 1, wherein the implantable medical device is a stent.

6. The implantable medical device according to claim 1, wherein the amphiphilic polymer is poly(n-butyl methacrylate-phosphorylcholine).

7. The implantable medical device according to claim 1, wherein the amphiphilic polymer is poly(ester amide)-phosphorylcholine.

8. The implantable medical device according to claim 1, wherein the amphiphilic polymer is polylactide-phosphorylcholine.

9. The implantable medical device according to claim 1, wherein the amphiphilic polymer is selected from the group consisting of polyethylene glycol-poly(caprolactone)-di- or tri-blocks.

10. The implantable medical device according to claim 1, wherein the amphiphilic polymer is selected from the group consisting of polyethylene glycol-polylactide di- or tri-blocks.

11. The implantable medical device according to claim 1, wherein the amphiphilic polymer is selected from the group consisting of polyethylene glycol-poly(lactide-glycolide) di- or tri-blocks.

* * * * *